(12) United States Patent
Meuleman

(10) Patent No.: US 10,450,605 B2
(45) Date of Patent: Oct. 22, 2019

(54) PYROPHOSPHOROLYTIC SEQUENCING

(71) Applicant: Illumina Cambridge Limited, Essex (GB)

(72) Inventor: Wouter Meuleman, Nr Saffron Walden (GB)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 0 days.

(21) Appl. No.: 15/847,362

(22) Filed: Dec. 19, 2017

(65) Prior Publication Data

US 2018/0105874 A1 Apr. 19, 2018

Related U.S. Application Data

(63) Continuation of application No. 14/286,447, filed on May 23, 2014.

(60) Provisional application No. 61/827,175, filed on May 24, 2013.

(51) Int. Cl.
*C12P 19/34* (2006.01)
*C12Q 1/6869* (2018.01)

(52) U.S. Cl.
CPC .................. *C12Q 1/6869* (2013.01)

(58) Field of Classification Search
CPC ............ C12Q 1/6869; C12Q 2521/319; C12Q 2521/525; C12Q 2565/631
USPC ........................................................ 435/91.2
See application file for complete search history.

(56) References Cited

U.S. PATENT DOCUMENTS

| | | | |
|---|---|---|---|
| 4,800,159 A | 1/1989 | Mullis et al. | |
| 4,962,020 A | 10/1990 | Tabor et al. | |
| 5,498,523 A * | 3/1996 | Tabor ...................... | C12N 9/16 435/194 |
| 6,107,023 A | 8/2000 | Reyes et al. | |
| 6,267,872 B1 | 7/2001 | Akeson et al. | |
| 6,268,146 B1 | 7/2001 | Shultz et al. | |
| 6,413,792 B1 | 7/2002 | Sauer et al. | |
| 6,627,067 B1 | 9/2003 | Branton et al. | |
| 6,916,665 B2 | 7/2005 | Bayley et al. | |
| 7,090,975 B2 | 8/2006 | Shultz et al. | |
| 7,444,053 B2 | 10/2008 | Schmidt et al. | |
| 7,582,490 B2 | 9/2009 | Golovchenko et al. | |
| 7,741,463 B2 | 6/2010 | Gormley | |
| 7,867,716 B2 | 1/2011 | Kang et al. | |
| 7,914,995 B2 | 3/2011 | Liu et al. | |
| 7,947,454 B2 | 5/2011 | Akeson et al. | |
| 8,071,536 B2 | 12/2011 | Bauer et al. | |
| 8,105,846 B2 | 1/2012 | Bayley et al. | |
| 2010/0120098 A1 | 5/2010 | Grunenwald et al. | |
| 2011/0229877 A1 | 9/2011 | Jayasinghe et al. | |
| 2011/0312529 A1 | 12/2011 | He et al. | |
| 2012/0055792 A1 | 3/2012 | Gundlach et al. | |

FOREIGN PATENT DOCUMENTS

| | | |
|---|---|---|
| WO | 90/12111 | 10/1990 |
| WO | 03/080861 | 10/2003 |
| WO | 2008/102120 | 8/2008 |
| WO | 2009/030953 | 3/2009 |
| WO | 2012/164270 | 12/2012 |
| WO | 2014/111723 | 7/2014 |

OTHER PUBLICATIONS

Dahl et al., The Journal of Biological Chemistry, 287(16), 13407-13421, Apr. 13, Year: 2012.*
Kasianowicz et al., Proc Natl Acad Sci USA, 93, 13770-13773, Year: 1996.*
Akeson et al., Biophys J, 77, 3227-3233, Year: 1999.*
Wanynu, Phy Life REv, 9 (2), 125-158, June Year: 2012.*
Akabayov et al., The Journal of Biological Chemistry, 286 (13), 29146-29157, 08 (Year: 2011).*
Akabayov, et al., "Pyrovanadolysis, a Pyrophosphorolysis-like Reaction Mediated by Pyrovanadate, $Mn^{2+}$, and DNA Polymerase of Bacteriophage T7," J. Biol. Chem., vol. 286, No. 33, published online, doi: 10.1074/jbc.M111.250944, Jun. 21, 2011, 29146-29157.
Cheley, et al., "Stochastic Sensing of Nanomolar Inositol 1,4,5-Trisphosphate with an Engineered Pore," Chemistry & Biology, vol. 9, Jul. 2002, 829-838.
Cherf, et al., "Automated forward and reverse ratcheting of DNA in a nanopore at 5-Å precision," Nat. Biotech., vol. 30, No. 4, published online, doi:10.1038/nbt.2147, Feb. 14, 2012, 344-348.
Clarke, et al., "Continuous base identification for single-molecule nanopore DNA sequencing," Nat. Biotech., vol. 4, published online, doi:10.1038/nnano.2009.12, Feb. 22, 2009, 265-270.
Deutscher, et al., "Enzymatic Synthesis of Deoxyribonucleic Acid: XXVIII. The Pyrophosphate Exchange and Pyrophosphorolysis Reactions of Deoxyribonucleic Acid Polymerase," J. Biol. Chem., vol. 244, No. 11, Jun. 10, 1969, 3019-3028.
Learish, et al., "Small-scale telomere repeat sequence content assay using pyrophosphorolysis coupled with ATP detection," Biotechniques, 33 (6), 2002, 1349-1353.

(Continued)

*Primary Examiner* — Cynthia B Wilder
(74) *Attorney, Agent, or Firm* — Illumina Cambridge Limited

(57) ABSTRACT

A method for determining the sequence of a target nucleic acid, including steps of contacting a target nucleic acid with a polymerase to sequentially remove nucleotide triphosphates from the target nucleic acid, wherein the nucleotide triphosphates that are removed have a variety of different base moieties; and distinguishing the different base moieties for the nucleotide triphosphates that are removed. Also provided is a apparatus including a nanopore positioned in a fluid impermeable barrier to form a passage through which a nucleotide triphosphate can pass from a first fluid reservoir to a second fluid reservoir, and a reaction mix in the first fluid reservoir that includes a polymerase, target nucleic acid having two strands, and pyrophosphorolytic concentration of pyrophosphate.

21 Claims, 3 Drawing Sheets

(56) References Cited

OTHER PUBLICATIONS

Manrao, et al., "Reading DNA at single-nucleotide resolution with a mutant MspA nanopore and phi29 DNA polymerase," Nat. Biotech., vol. 30, No. 4, Apr. 2012, 349-353.
Montal, et al., "Formation of Bimolecular Membranes from Lipid Monolayers and a Study of Their Electrical Properties," Proc. Nat. Acad. Sci., vol. 69, No. 12, Dec. 1972, 3561-3566.
Patel, et al., "Pre-steady-state kinetic analysis of processive DNA replication including complete characterization of an exonuclease-deficient mutant," Biochemistry, vol. 30 (2), Jan. 1991, 511-525.
Sram, et al., "Microarray-based DNA re-sequencing using 3' blocked primers," Analytical Biochemistry, 374 (1), 2007, 41-47.
International Search Report in International Application No. PCT/EP2014/060588, dated Sep. 1, 2014, 13 pages.
Dahl et al., "Direct Observation of Translocation in Individual DNA Polymerase Complexes", The Journal of Biological Chemistry, vol. 287, No. 16, Apr. 13, 2012, 13407-13421.
Rhee, "Nanopore Sequencing Technology: Nanopore Preparations", TRENDS in Biotechnology 25(4), exhibit submitted Jun. 29, 2015 in support of Patent Owners' Suppl Resp for U.S. Patent Trial and Appeal Board.
Case No. IPR2014-00513, *Oxford Nanopore Technologies Ltd.* v. *Univ of Washington and UAB Research Foundation,* Apr. 2007, 8 pages.

\* cited by examiner

PYROPHOSPHOROLYTIC SEQUENCING

CROSS-REFERENCE TO RELATED APPLICATIONS

This application is a continuation of U.S. patent application Ser. No. 14/286,447, filed May 23, 2014, which is based on, and claims the benefit of, U.S. Provisional Application No. 61/827,175, filed May 24, 2013, which is incorporated herein by reference.

BACKGROUND

This disclosure relates generally to nucleic acid analysis, and more specifically to nucleic acid synthesis using nanopores.

Currently available commercial platforms for sequencing DNA are relatively costly. These platforms use a 'sequencing by synthesis' approach, so called because DNA polymers are synthesized while detecting the addition of each monomer (i.e. nucleotide) to the growing polymer structure. Because a template DNA strand strictly directs synthesis of a new DNA polymer, one can infer the sequence of the template DNA from the series of nucleotide monomers that were added to the growing strand during the synthesis. The ability to detect monomer additions is facilitated by specially engineered variants of the biochemical components that normally carry out DNA synthesis in biological systems. These engineered components are expensive to make and are consumed in relatively large amounts during sequencing by synthesis. Furthermore, monitoring the reaction uses relatively expensive hardware such as lasers, detection optics and complex fluid delivery systems. The most successful commercial platforms to date also require expensive reagents and hardware to amplify the DNA templates before sequencing by synthesis can even begin.

Other sequencing methods have been considered in order to reduce cost, increase throughput, and/or simplify the process. One of these approaches is based on threading a single strand of DNA through a nanopore and identifying its sequence from the variation in the ionic current flowing through the pore as the strand is threaded. An alternative to this 'nanopore-strand' sequencing approach is 'nanopore-exonuclease' sequencing, which involves exonuclease catalyzed removal of nucleotide monophosphates, one at a time, from a DNA strand and sequentially passing the released nucleotide monophosphates through a nanopore. However, the resulting variations in the ionic current flowing through the nanopores are quite small and it is difficult to distinguish one nucleotide from another. Attempts have been made to modify the DNA before digestion or to modify the nucleotide monophosphates once they have been released. However despite these efforts, nanopore-exonuclease sequencing has not yet been demonstrated at a commercially viable level to date.

Thus, there exists a need for more cost effective, rapid and convenient platforms that provide an alternative to those currently available for sequencing nucleic acids. The present disclosure addresses this need and provides other advantages as well.

BRIEF SUMMARY

The present disclosure provides a method for determining the sequence of a target nucleic acid. The method can include the steps of (a) providing a target nucleic acid; (b) contacting the target nucleic acid with a polymerase to sequentially remove nucleotide triphosphates from the target nucleic acid, wherein the nucleotide triphosphates that are removed have a variety of different base moieties; and (c) distinguishing the different base moieties for the nucleotide triphosphates that are removed, thereby determining the sequence of the target nucleic acid.

In some embodiments a method for determining the sequence of a target nucleic acid can be carried out using the steps of (a) providing a target nucleic acid having two strands; (b) contacting the target nucleic acid with a polymerase under conditions to sequentially remove nucleotides from the first of the two strands by pyrophosphorolysis, thereby sequentially producing nucleotide triphosphates having a variety of different base moieties; and (c) distinguishing the different base moieties for the sequentially produced nucleotide triphosphates, thereby determining the sequence of the target nucleic acid.

The present disclosure also provides a apparatus that includes (a) a fluid impermeable barrier separating a first fluid reservoir from a second fluid reservoir; (b) a nanopore positioned in the fluid impermeable barrier to form a passage through which a nucleotide triphosphate can pass from the first fluid reservoir to the second fluid reservoir; and (c) a reaction mix in the first fluid reservoir, the reaction mix comprising a polymerase, target nucleic acid having two strands, and pyrophosphorylitic concentration of pyrophosphate.

DETAILED DESCRIPTION

Figure 1:
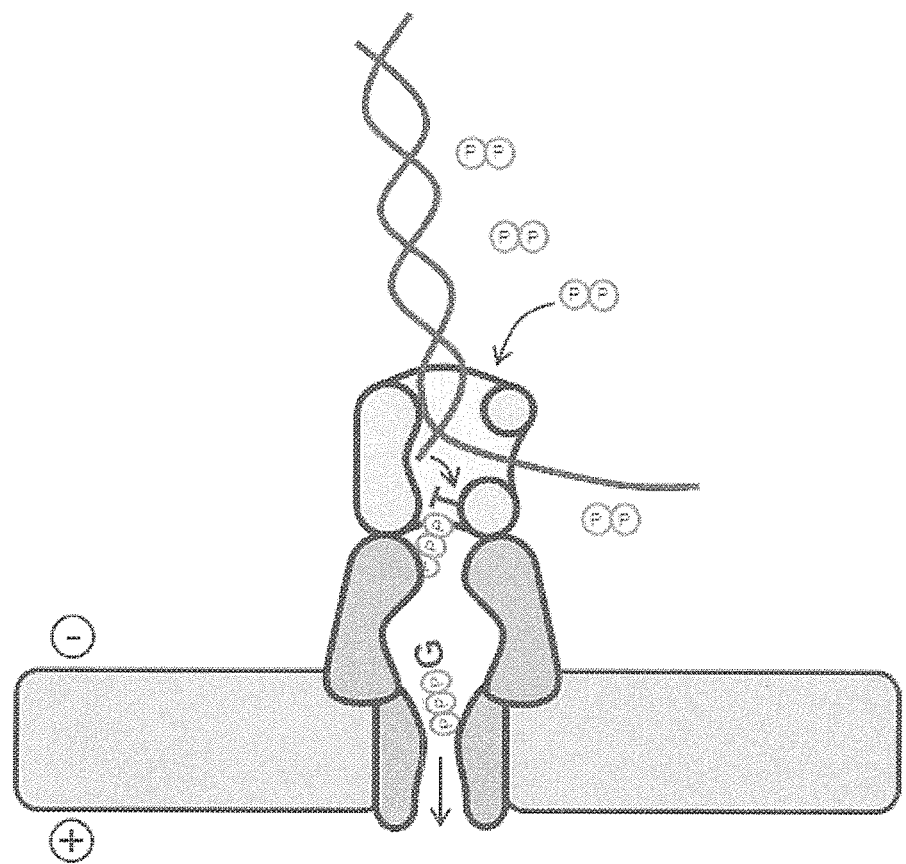
FIG. 1 shows a diagram of a pyrophosphorolytic sequencing reaction using a polymerase attached to a nanopore.

The present disclosure provides a method of sequencing nucleic acids in a reverse fashion compared to standard sequencing by synthesis (SBS) techniques. In particular embodiments, the method of the present disclosure exploits a catalytic function of polymerase known as pyrophosphorolysis that is typically maligned as the culprit for unwanted artifacts in SBS techniques. Pyrophosphorolysis results in the removal of nucleotide triphosphates from a nucleic acid strand by a polymerase, and as such is the reverse of the polymerization reaction that drives standard SBS techniques.

Pyrophosphorolysis can be distinguished from exonuclease activity (which is present in some polymerases), for example, based on the different catalytic mechanism for the two reactions, different active sites in the polymerase structure where the two reactions occur, and the different products for the reactions. Regarding the catalytic mechanism and active site differences, it is known that exonuclease activity can be removed from many polymerase species by deletion of certain domains, whereas pyrophosphorolysis activity is believed to be catalyzed by the same domain that catalyzes polymerization. Furthermore, the reaction cycle catalyzed by exonuclease is the conversion of $DNA_n$ (DNA of length n) to $DNA_{n-1}$ (DNA that is one nucleotide shorter than DNA of length n) and a nucleotide monophosphate. In contrast, a cycle of pyrophosphorolysis produces $DNA_{n-1}$ and a nucleotide triphosphate from $DNA_n$ and pyrophosphate. Notably, pyrophosphate is consumed in a pyrophosphorolysis reaction but is not consumed in an exonuclease reaction.

Particular embodiments of the pyrophosphorolytic sequencing methods utilize nanopore detection. Nanopores can be used to sequentially detect the nucleotide triphosphates that are released from a nucleic acid in order to determine the sequence of the nucleic acid. Such embodiments provide a combination of advantages that are typically only partially satisfied by nanopore-exonuclease sequencing or nanopore-strand sequencing. Specifically, the pyrophosphorolytic sequencing methods of the present disclosure address some of the challenges incurred in nanopore-exonuclease sequencing, namely low capture and detection probabilities, while retaining its main advantage over strand sequencing, namely single base resolution. This advantage derives from the fact that the affinity of nanopores for nucleotide monophosphates is rather weak (on the order of micromolar affinity), even in the presence of an am6-cyclodextrin adaptor that has been used to improve signal in some nanopore systems. See Clarke et al., *Nat. Nanotechnol.* April; 4(4):265-70 (2009), which is incorporated herein by reference. For successful distinction of different nucleotide types in a sequencing context, nanomolar range affinity is desired. ATP has an affinity that is in a good range, even without the use of an adaptor in the pore. See Cheley et al., *Chem. Biol.* 9, 829-838 (2002), which is incorporated herein by reference. Without wishing to be bound by theory, it is postulated that the improved affinity of ATP over nucleotide monophosphate is due to the triple negative charge carried by ATP, which may cause it to bind more strongly inside the nanopore. Furthermore, the triple negative charge may aid capturing of the molecule in the presence of an electric field, especially when the field is very weak, as is the case outside of the nanopore where the nucleotides are actually released.

In addition to the enhanced capture and detection of nucleotide triphosphates, there are a number of other advantages that can be provided by embodiments set forth herein, such as the use of a polymerase as opposed to an exonuclease. Polymerases have been shown to form a good "fit" with nanopores for the purpose of nanopore-strand sequencing (Cherf et al., *Nat. Biotech.* 30:344-348 (2012); Manrao et al., *Nat. Biotech.* 30:349-353 (2012), each of which is incorporated herein by reference). A similarly good fit is yet to be demonstrated with exonucleases. Furthermore, the substrate for polymerases is double stranded DNA which generally does not enter the nanopore. In contrast, single stranded DNA, the substrate for most exonucleases, can pose the problem of entering and blocking the nanopore. Finally, unlike in either exonuclease-based sequencing or polymerase-based strand sequencing, the rate of a pyrophosphorolytic sequencing reaction can be controlled by tuning the pyrophosphate concentration.

Terms used herein will be understood to take on their ordinary meaning unless specified otherwise. Examples of several terms used herein and their definitions are set forth below.

As used herein, the term "attached" is intended to mean connected by forces that prevent separation by diffusion. The term can include connections that are covalent or non-covalent in nature. For example two proteins can be covalently attached through their primary sequence (e.g. a peptide linkage or protein fusion) or between their primary sequences (e.g. a disulfide linkage or chemical crosslink via amino acid R groups). Two proteins can be non-covalently attached, for example, via one or more of hydrogen bonds, ionic bonds, van der Waals forces, hydrophobic bonds or the like.

As used herein, the term "each," when used in reference to a collection of items, is intended to identify an individual item in the collection but does not necessarily refer to every item in the collection. Exceptions can occur if explicit disclosure or context unambiguously dictates otherwise.

As used herein, the term "exonuclease activity" is intended to mean hydrolysis of the phosphodiester bond that attaches a nucleotide to the end of a nucleic acid of length n to produce a nucleotide monophosphate and a nucleic acid of length n−1. The hydrolysis can occur at the bond that attaches the 5' nucleotide to the nucleic acid (i.e. 5' to 3' exonuclease activity) or at the bond that attaches the 3' nucleotide to the nucleic acid (i.e. 3' to 5' exonuclease activity).

As used herein, the term "fluid impermeable barrier" is intended to mean anything that prevents passage of a fluid. For example, a fluid impermeable barrier can be present between two reservoirs such that a fluid in the first reservoir is separated from the fluid in the second reservoir, and the fluids do not mix. A fluid impermeable barrier can include a pore or opening that allows passage of a fluid that is otherwise obstructed by the remainder of the barrier. In particular embodiments, the fluid can be an aqueous fluid and the barrier can be impermeable to aqueous fluids.

As used herein, the term "lacks exonuclease activity" is intended to mean having no measurable exonuclease activity. For example, a polymerase or other agent that lacks 3' to 5' exonuclease activity will have no measurable 3' to 5' exonuclease activity. Similarly, a polymerase or other agent that lacks 5' to 3' exonuclease activity will have no measurable 5' to 3' exonuclease activity. Polymerases known in the art as "exo minus" (or "exo-") whether naturally occurring or engineered are non-limiting examples of polymerases that lack exonuclease activity. Known variants include those that are 5' to 3' exo minus and/or 3' to 5' exo minus.

As used herein, the term "nanopore" is intended to mean a small hole that allows passage of nucleotide triphosphates across an otherwise impermeable barrier. The barrier is typically an electrically insulating layer and the nanopore typically permits ions to flow from one side of the barrier to the other, driven by an applied potential. The nanopore preferably permits nucleotides to flow through the nanopore lumen along the applied potential. The nanopore may also allow a nucleic acid, such as DNA or RNA, to be pushed or pulled through the lumen of the nanopore. However, in particular embodiments the nanopore need not allow passage of a double stranded or single stranded nucleic acid. A nanopore used in a particular embodiment can have a minimum lumen diameter of no more than 10 nm, 5 nm, 4 nm, 3 nm, 2 nm, 1 nm, 0.5 nm or less. One type of nanopore is a "protein nanopore" which is a polypeptide or a collection of polypeptides that forms the small hole to allow passage of nucleotide triphosphates across a barrier such as a lipid bilayer. Examples of protein nanopores include alpha hemolysin nanopore, *mycobacterium smegmatis* porin A (MspA) and variants thereof. Another type of nanopore is a "solid state nanopore" which is a small hole fabricated through a solid material. The solid material can be, for example, graphene or silicon.

As used herein the term "nucleotide" is intended to include ribonucleotides, deoxynucleotides or analogs thereof. For example the term is used herein to generally refer to a nucleoside moiety (whether ribose, deoxyribose, or analog thereof) including a base moiety and optionally attached to one or more phosphate moieties. Exemplary nucleotides include, but are not limited to, ribonucleotide monophosphate (sometimes referred to as a ribonucleoside monophosphate), ribonucleotide diphosphate (sometimes referred to as a ribonucleoside diphosphate), ribonucleotide triphosphate (sometimes referred to as a ribonucleoside triphosphate), deoxynucleotide monophosphate (sometimes referred to as a deoxynucleoside monophosphate), deoxynucleotide diphosphate (sometimes referred to as a deoxynucleoside diphosphate) and deoxynucleotide triphosphate (sometimes referred to as a deoxynucleoside triphosphate). For clarity when wishing to distinguish RNA components from DNA components, the term "ribonucleotide" can be used to specify RNA nucleotides, such as ribouridine triphosphate, riboguanidine triphosphate, ribocytidine triphosphate or riboadenosine triphosphate; and the term "deoxynucleotide" can be used to specify DNA nucleotides, such as deoxythymidine triphosphate, deoxyguanidine triphosphate, deoxycytidine triphosphate and deoxyadenosine triphosphate. In particular embodiments, the nucleotides are 'extendable', for example, lacking an extension blocking moiety at the 3' hydroxyl or at any other position on the nucleotide.

As used herein, the term "pyrophosphorolysis" is intended to mean reaction between pyrophosphate and the 3'-nucleotide unit of a nucleic acid to release the nucleotide in the form of the corresponding nucleotide triphosphate. A further product of the reaction is the nucleic acid lacking the corresponding nucleotide (i.e. the reaction converts a nucleic acid of length n to a nucleic acid of length n−1). The reaction is typically catalyzed by a polymerase and is the reverse of the polymerization reaction carried out by the polymerase under standard biological conditions.

As used herein, the term "pyrophosphorolytic concentration," when used in reference to pyrophosphate, is intended to mean a concentration of pyrophosphate that causes a pyrophosphorolysis reaction to occur at a substantial level. For example, a pyrophosphorylitic concentration of pyrophosphate can result in a polymerase displaying a higher rate of pyrophosphorolysis than polymerization. Thus, a pyrophosphorylitic concentration of pyrophosphate can result in a substantial reversal of polymerization activity that would otherwise be catalyzed by a polymerase.

As used herein, the term "reservoir" is intended to mean a receptacle or chamber for holding or restricting the flow of fluid. A reservoir can be fully enclosed, at least temporarily. Alternatively, a reservoir can be partially enclosed, for example, having one or more opening (e.g. one or more inlets or outlets). A fluid may flow through a reservoir, for example, in embodiments where the reservoir is in a flow cell.

As used herein, the term "species" is used to identify molecules that share the same chemical structure. For example, a mixture of nucleotides can include several dCTP molecules. The dCTP molecules will be understood to be the same species as each other. Similarly, individual DNA molecules that have the same sequence of nucleotides are the same species.

The embodiments set forth below and recited in the claims can be understood in view of the above definitions.

The present disclosure provides a method for determining the sequence of a target nucleic acid. The method can include the steps of (a) providing a target nucleic acid; (b) contacting the target nucleic acid with a polymerase to sequentially remove nucleotide triphosphates from the target nucleic acid, wherein the nucleotide triphosphates that are removed have a variety of different base moieties; and (c) distinguishing the different base moieties for the nucleotide triphosphates that are removed, thereby determining the sequence of the target nucleic acid.

In some embodiments a method for determining the sequence of a target nucleic acid can be carried out using the steps of (a) providing a target nucleic acid having two strands; (b) contacting the target nucleic acid with a polymerase under conditions to sequentially remove nucleotides from the first of the two strands by pyrophosphorolysis, thereby sequentially producing nucleotide triphosphates having a variety of different base moieties; and (c) distinguishing the different base moieties for the sequentially produced nucleotide triphosphates, thereby determining the sequence of the target nucleic acid.

An exemplary embodiment is shown in FIG. 1. As shown, a polymerase binds to a double stranded DNA molecule and, in the presence of excess pyrophosphate, catalyzes a pyrophosphorolysis reaction to release nucleotide triphosphates from the 3' end of one of the strands. In this example, a deoxyguanidine triphosphate has been produced followed by a deoxythymidine triphosphate. The polymerase is coupled to a nanopore and the deoxyguanidine triphosphate is in the lumen of the nanopore, whereas the deoxythymidine triphosphate is in the process of being released into the nanopore lumen. As such the deoxynucleotide triphosphates enter the nanopore sequentially, in the same order that they were released from the DNA strand by the pyrophosphorolytic action of the polymerase. The deoxynucleotide triphosphates have a net negative charge due to the triphosphates and are driven through the nanopore by a potential across the membrane (as indicated by the positive sign on the side of the membrane where pyrophosphorolysis occurs and a negative sign on the opposite side of the membrane). Typically, reagent nucleotide triphosphates are not present in a pyrophosphorolysis reaction. In some cases, trace amounts of nucleotide triphosphates can be present, but at amounts that do not substantially catalyze a forward primer extension reaction by polymerase. Thus, in most embodiments the only nucleotide triphosphates that are substantially present in a pyrophosphorolysis reaction are those produced by the catalytic action of the polymerase on the nucleic acid.

Figure 2:
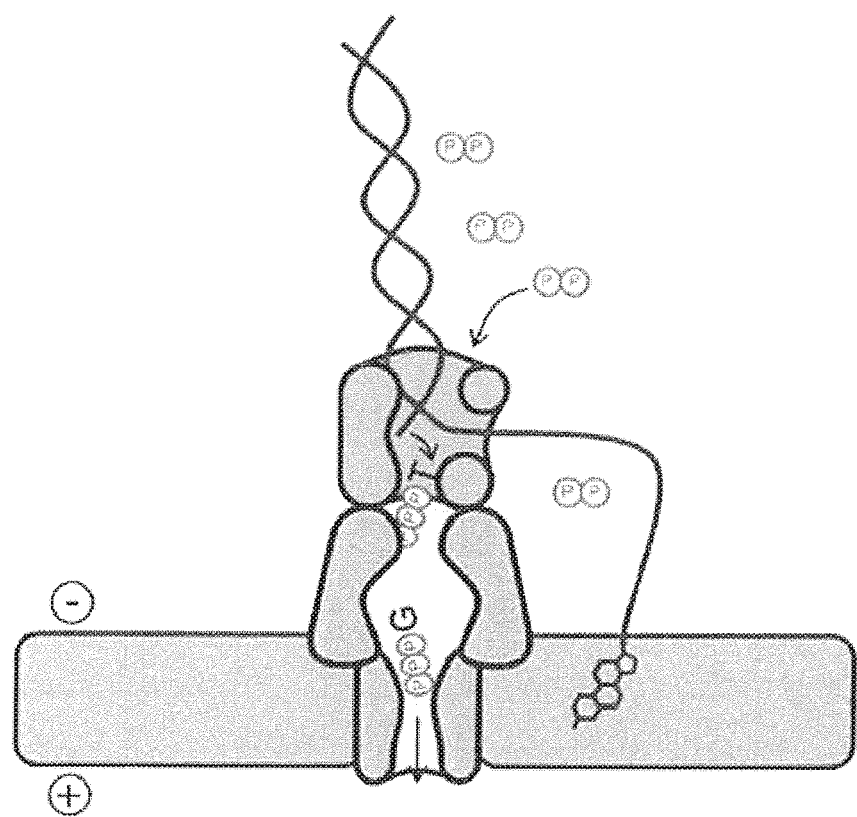
FIG. 2 shows a diagram of a pyrophosphorolytic sequencing reaction using a polymerase attached to a nanopore and a template nucleic acid attached to a fluid impermeable barrier.

A similar reaction is exemplified in FIG. 2 except that the template strand (i.e. the strand that is not being cleaved by pyrophosphorolysis) is bound to the membrane. In this case, the template strand has a covalently attached sterol moiety (e.g. cholesterol) that binds to the hydrophobic interior of the membrane's lipid bilayer.

A method of the present disclosure can be used with any of a variety of target nucleic acids. The target nucleic acid can have a naturally occurring structure as found for example in DNA or RNA. DNA naturally contains monomers having thymine, guanine, cytosine, or adenine bases. A DNA strand that is subjected to pyrophosphorolysis can produce deoxythymidine triphosphate, deoxyguanidine triphosphate, deoxycytidine triphosphate and deoxyadenosine triphosphate, respectively. DNA can also contain some variants of the four nucleotide bases such as 5-methyl cytosine, 5-hydroxymethylcytosine and other methylated bases. Deoxynucleotide triphosphates having these variant bases can be produced and/or detected using a method or apparatus set forth herein. For example, the presence or absence of methylation on cytosine can be distinguished to facilitate epigenetic analyses. RNA naturally contains monomers having uracil, guanine, cytosine, or adenine bases. An RNA strand that is subjected to pyrophosphorolysis can produce ribouridine triphosphate, riboguanidine triphosphate, ribocytidine triphosphate or riboadenosine triphosphate, respectively.

A nucleic acid can include non-naturally occurring modifications such as non-native bases, modifications to the phosphate moieties or modifications to the sugar moieties. Exemplary non-native bases that can be included in a nucleic acid, whether having a native backbone or analog structure, include, without limitation, inosine, xathanine, hypoxathanine, isocytosine, isoguanine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like.

Non-native bases can be selected, for example, to impart larger or smaller size, or to impart increased or decreased charge, so as to influence the ability of the resulting nucleotide triphosphate analogs to be distinguished by a nanopore or other detection component. Similarly, such bases can be beneficial if selected to impart a desired rate of pyrophosphorolysis. Non-native bases can be incorporated into a nucleic acid using known methods such as amplification or replication of a template nucleic acid in the presence of the nucleotide analogs. One or more of the resulting nucleic acid copies can then be used as target nucleic acid(s) in apparatus or sequencing method set forth herein.

In particular embodiments, a nucleic acid that is used in a method or apparatus herein will lack one or more of the non-native bases or other non-native moieties set forth herein. For example, in particular embodiments the methods are not used to remove a terminator nucleotide from the 3' end of a nucleic acid strand. Accordingly, in some embodiments, an apparatus or method may not include any nucleic acid(s) having a terminator nucleotide at its 3' end. Alternatively or additionally, in some embodiments, an apparatus or method may not include any terminator nucleotide(s).

As exemplified in FIG. 1 and elsewhere herein, a target nucleic acid can be double stranded DNA, for example, when using a DNA polymerase for pyrophosphorolysis. A heteroduplex, formed between a DNA strand and RNA strand, can also be used. For example, an RNA polymerase can be used to catalyze pyrophosphorolysis at the 3' end of an RNA strand that is hybridized to a DNA template strand, thereby producing ribonucleotide triphosphates.

A nucleic acid that is used in a method or apparatus herein can be isolated from a biological source and used directly or processed to produce an amplified or modified product. Alternatively a synthetic nucleic acid can be used, again, directly or after processing. Processing can include, for example, one or more of isolation from native components, cleavage to form fragments, amplification (e.g. via PCR, Rolling Circle or other known techniques), ligation of adapter sequences or tag sequences, tagmentation using a transposon, or "sample preparation" methods used prior to nucleic acid sequencing techniques. Useful processing techniques are known in the art as set forth, for example, in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

Examples of sample preparation methods that can be used to process nucleic acids prior to pyrophosphorolysis-based sequencing include methods that have been developed for whole genome amplification or whole exome amplification in combination with massively parallel sequencing techniques. For example, commercially available sample preparation techniques from Illumina, Inc. (San Diego, Calif.), Life Technologies (Carlsbad, Calif.), 454 Life Sciences (a subsidiary of Roche, Basel, Switzerland) or New England Biolabs (Ipswich, Mass.) can be used. Further useful sample preparation methods that can be used are described, for example, in U.S. Pat. Nos. 6,107,023 or 7,741,463; or US Pat. App. Pub. No. 2010/0120098 A1, each of which is incorporated herein by reference. Targeted sample preparation methods can be used as well in order to isolate a subset of the sequence content of a complex sample for subsequent sequencing. Exemplary commercial methods that can be used for targeted capture of a subset of nucleic acid fragments include, but are not limited to SureSelect™ kits (Agilent, Santa Clara, Calif.), TruSeq Enrichment Kits (Illumina, Inc., San Diego, Calif.) or Nextera® Enrichment Kits (Illumina, Inc., San Diego, Calif.).

Nucleic acids can be isolated from any of a variety of sources including, without limitation, a mammal such as a rodent, mouse, rat, rabbit, guinea pig, ungulate, horse, sheep, pig, goat, cow, cat, dog, primate, human or non-human primate; a plant such as *Arabidopsis thaliana*, corn (*Zea mays*), sorghum, oat (*oryza sativa*), wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish (*Danio rerio*); a reptile; an amphibian such as a frog or *Xenopus laevis*; a *dictyostelium discoideum*; a fungi such as *pneumocystis carinii, Takifugu rubripes*, yeast, *Saccharamoyces cerevisiae* or *Schizosaccharomyces pombe*; or a *plasmodium falciparum*. Nucleic acids can also be derived from smaller genomes such as those from a prokaryote such as a bacterium, *Escherichia coli, staphylococci* or *mycoplasma pneumoniae*; an archae; a virus such as Hepatitis C virus or human immunodeficiency virus; or a viroid.

Any of a variety of polymerases can be used in a method or apparatus set forth herein including, for example, protein-based enzymes isolated from biological systems and functional variants thereof. Reference to a particular polymerase, such as those exemplified below, will be understood to include functional variants thereof unless indicated otherwise. Examples of useful polymerases include DNA polymerases and RNA polymerases. Exemplary DNA polymerases include those that have been classified by structural homology into families identified as A, B, C, D, X, Y, and RT. DNA Polymerases in Family A include, for example, T7 DNA polymerase, eukaryotic mitochondrial DNA Polymerase γ, *E. coli* DNA Pol I, *Thermus aquaticus* Pol I, and *Bacillus stearothermophilus* Pol I. DNA Polymerases in Family B include, for example, eukaryotic DNA polymerases α, δ, and ε; DNA polymerase ζ; T4 DNA polymerase, Phi29 DNA polymerase, and RB69 bacteriophage DNA polymerase. Family C includes, for example, the *E. coli* DNA Polymerase III alpha subunit. Family D includes, for example, polymerases derived from the Euryarchaeota subdomain of Archaea. DNA Polymerases in Family X include, for example, eukaryotic polymerases Pol β, pol σ, Pol λ, and Pol μ, and *S. cerevisiae* Pol4. DNA Polymerases in Family Y include, for example, Pol η, Pol iota, Pol kappa,

*E. coli* Pol IV (DINB) and *E. coli* Pol V (UmuD'2C). The RT (reverse transcriptase) family of DNA polymerases includes, for example, retrovirus reverse transcriptases and eukaryotic telomerases. Exemplary RNA polymerases include, but are not limited to, viral RNA polymerases such as T7 RNA polymerase; Eukaryotic RNA polymerases such as RNA polymerase I, RNA polymerase II, RNA polymerase III, RNA polymerase IV, and RNA polymerase V; and Archaea RNA polymerase.

The above classifications are provided for illustrative purposes. It will be understood that variations in the classification system are possible. For example, in at least one classification system Family C polymerases have been categorized as a subcategory of Family X. Furthermore, polymerases can be classified according to other characteristics, whether functional or structural, that may or may not overlap with the structural characteristics exemplified above. Some exemplary characteristics are set forth in further detail below.

Many polymerases have an intrinsic 3' to 5' proofreading exonuclease activity which can be useful for some embodiments. Polymerases that substantially lack 3' to 5' proofreading exonuclease activity are preferred in some embodiments, for example, in most sequencing embodiments. Absence of exonuclease activity can be a wild type characteristic or a characteristic imparted by a variant or engineered polymerase. For example, exo minus Klenow fragment is a mutated version of Klenow fragment that lacks 3' to 5' proofreading exonuclease activity. Klenow fragment and its exo minus variant can be useful in a method or apparatus set forth herein. Polymerases that catalyze pyrophosphorolysis, the direct reversal of polymerization in the same active site, are particularly useful.

Depending on the embodiment that is to be used, a polymerase can be either thermophilic or heat inactivatable. Thermophilic polymerases are typically useful for high temperature conditions or in thermocycling conditions such as those employed for polymerase chain reaction (PCR) techniques. Examples of thermophilic polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase. Most polymerases isolated from non-thermophilic organisms are heat inactivatable. Heat inactivation can be useful to stop a sequencing reaction set forth herein. The reaction can optionally be re-started by adding a new supply of polymerase to the reaction at the appropriately permissive temperature. Examples of heat inactivatable polymerases are those from phage. It will be understood that polymerases from any of a variety of sources can be modified to increase or decrease their tolerance to high temperature conditions.

An engineered variant of a polymerase having increased pyrophosphorolysis activity can be used. Exemplary variants are those that have been created for use in PCR techniques including, but not limited to the variants described in U.S. Pat. No. 8,071,536, which is incorporated herein by reference.

A polymerase can be induced to sequentially remove nucleotides from one of two nucleic acid strands by pyrophosphorolysis in a method set forth herein. The polymerase can be placed under conditions for pyrophosphorolysis to occur. For example, the polymerase can be contacted with a double stranded nucleic acid and a pyrophosphorolytic concentration of pyrophosphate. Any concentration of pyrophosphate that causes a pyrophosphorolysis reaction to occur at a substantial level can be used including, but not limited to, at least about 100 µM pyrophosphate. Higher concentrations of pyrophosphate can be employed, for example, to drive pyrophosphorolysis at a faster rate. Accordingly, a concentration of at least about 250 µM pyrophosphate, at least about 500 µM pyrophosphate, at least about 750 µM pyrophosphate, at least about 1 mM pyrophosphate, at least about 2 mM pyrophosphate, at least about 5 mM pyrophosphate, at least about 10 mM pyrophosphate, at least about 20 mM pyrophosphate or higher can be used.

The ability to alter the rate of pyrophosphorolysis is an advantage for tuning the rate of the sequencing reaction, for example, to accommodate an optimal or desired rate of nucleotide triphosphate detection for a given detection device. For example, the rate of pyrophosphorolysis can be decreased by using a lower concentration of pyrophosphate than those set forth above. Thus, as an alternative or addition to the threshold concentrations set forth above, a maximum concentration of pyrophosphate present in a apparatus or method set forth herein can be at most about 20 mM pyrophosphate, at most about 10 mM pyrophosphate, at most about 5 mM pyrophosphate, at most about 2 mM pyrophosphate, at most about 1 mM pyrophosphate, at most about 750 µM pyrophosphate, at most about 500 µM pyrophosphate, at most about 250 µM pyrophosphate, at most about 100 µM pyrophosphate, or less.

Reagent nucleotide triphosphates are typically absent under pyrophosphorolysis conditions. Thus, in most embodiments the only nucleotide triphosphates that are substantially present in a pyrophosphorolysis reaction are those produced by the catalytic action of the polymerase on the nucleic acid. If nucleotide triphosphates are present under pyrophosphorolysis conditions, the nucleotide triphosphates will be present at what can be considered a non-catalytic concentration. A non-catalytic concentration of nucleotide triphosphate is a concentration that is insufficient to allow substantial or detectable polymerase extension activity to occur. For example, a non-catalytic concentration of nucleotide triphosphate is a concentration that is substantially below the association binding constant for binding of the nucleotide triphosphates to polymerase. Accordingly, pyrophosphorolysis can be carried out by contacting a polymerase with a double stranded nucleic acid in the presence of a pyrophosphorolytic concentration of pyrophosphate and no more than a non-catalytic concentration of nucleotide triphosphate.

Exemplary conditions for inducing pyrophosphorolysis that can be used herein are set forth in Patel et al. *Biochem.* 30:511-525 (1991), or U.S. Pat. Nos. 7,090,975; 7,914,995 or 8,071,536, each of which is incorporated herein by reference. In several cases these references describe reactions that also include components used for extension of a nucleic acid. It will be understood that extension is not utilized in particular embodiments of the present disclosure. One or more of the components that are described in Patel et al. *Biochem.* 30:511-525 (1991) or U.S. Pat. Nos. 7,090, 975; 7,914,995 or 8,071,536, including, for example, components used for polymerase extension reaction, can be excluded from a method or apparatus set forth herein.

Buffers, salts, metal ions, glycerol, DMSO and other components typically included in polymerase storage or reaction mixtures can be included in a apparatus or method of the present disclosure, as desired. The quantities and amounts of components to be included will be apparent to those skilled in the art or determinable, for example, via routine titration techniques.

A beneficial aspect of some embodiments is the ability to stop or pause the sequencing method by altering the reaction conditions to inhibit pyrophosphorolysis. The sequencing method can then optionally be restarted by altering the reaction conditions to allow pyrophosphorolysis to resume. Any of a variety of the reaction conditions set forth herein, or in the references cited herein, can be altered between paused pyrophosphorolysis and resumed pyrophosphorolysis, thereby allowing an effective toggle between paused and active sequencing, respectively.

In particular embodiments, a method of the present disclosure can include a step of pausing the sequential production of nucleotide triphosphates by removing pyrophosphate from contact with a polymerase that is catalyzing pyrophosphorolysis, followed by a step of resuming the sequential production of the nucleotide triphosphates by contacting the polymerase with pyrophosphate. Pyrophosphate can be delivered to a reaction using techniques appropriate for the fluid system being used including, for example, pipetting fluid aliquots, movement of fluid boluses under positive or negative pressure (e.g. via pumps or gravity), electrophoresis, isotachophoresis, droplet manipulation (e.g. electrowetting) or the like. Similar fluidic techniques can be used to remove pyrophosphate, for example, by displacement and/or replacement with a wash solution. Of course, such fluidic techniques can be used to add or remove other components used in the methods and apparatus set forth herein.

Alternatively or additionally to the fluidic methods set forth above, pyrophosphate can be removed from the reaction by sequestration, degradation or inactivation. For example, physical manipulations can be used such as adsorption to a sequestering agent, or degradation by heat, light or electricity. Chemical methods can be used to modify the structure or activity of pyrophosphate or to degrade the molecule. Enzymatic methods can also be used such as degradation by pyrophosphatase, as shown for PCR reactions in U.S. Pat. Nos. 4,800,159 and 5,498,523 and for gel based sequencing reactions in U.S. Pat. No. 4,962,020, each of which is incorporated herein by reference.

Alternatively or additionally to the techniques set forth above, pyrophosphorolysis can be stopped or paused by removing other reaction components. For example, polymerase can be removed from a reaction and optionally replaced or returned to an active state. For example, polymerase can be removed by fluidic, sequestration, degradation or inactivation methods such as those exemplified above for pyrophosphate. In particular embodiments, a heat sensitive (non-thermophilic) polymerase can be used in a pyrophosphorolysis reaction and then heat inactivated. Similarly, a polymerase can be degraded by chemical modification or enzymatic degradation (e.g. via a protease). Whether degraded by physical, chemical or enzymatic techniques, the spent polymerase can be washed away and then pyrophosphorolysis can be resumed by addition of new polymerase to the nucleic acid being sequenced. Polymerase activity can also be toggled by addition and removal of inhibitors, toggling between permissive and non-permissive temperatures for heat stable polymerases, or presence and absence of a sequestering agent or competitive substrate. Pyrophosphorolysis can also be stopped and started by denaturation and renaturation, respectively, of the nucleic acid that is being sequenced.

Although methods and apparatus have been exemplified herein for embodiments that use pyrophosphate to drive pyrophosphorolysis, it will be understood that analogs of pyrophosphate can be used instead. An exemplary analog is pyrovanadate, which can be used, for example, as described in Akabayov et al. *J. Biol. Chem.* 286:29146-29157 (2011), which is incorporated herein by reference. As further examples, analogs of pyrophosphate having additional moieties can be used. Generally pyrophosphate analogs are selected that do not entirely inhibit pyrophosphorolysis or passage of the resulting nucleotide triphosphates, or analogs thereof, through a nanopore. However, pyrophosphate analogs can alter characteristics of pyrophosphorolysis and/or nanopore detection. For example, it may be beneficial to use a pyrophosphate analog to slow down or speed up pyrophosphorolysis to provide a desired or optimal detection rate. Similarly, analogs of nucleotide triphosphates that result when a pyrophosphate analog is used in a pyrophosphorolysis reaction can also impart desired characteristics for nanopore detection. For example, moieties that alter charge or size, compared to diphosphate alone, can increase or decrease the rate of passage of nucleotide triphosphate analogs through a nanopore, or otherwise alter interactions of the nucleotide triphosphate analogs with the nanopore, to provide improved sequencing results.

However, in some embodiments a method or apparatus of the present disclosure will exclude pyrophosphate having any added moieties. For example, pyrophosphate that lacks an optically detectable moiety, such as a fluorescent moiety, can be used.

In particular embodiments, nucleotide triphosphates are detected using nanopores. For example, nucleotide triphosphates that are sequentially removed from a nucleic acid via pyrophosphorolysis can be passed through a nanopore for detection. By use of an appropriate nanopore, different base moieties of the nucleotide triphosphates can be distinguished to allow sequence detection. Generally an apparatus can be used that includes a first and a second compartment separated by a physical barrier, wherein the barrier has one or more nanopores. The first compartment can include components used for a pyrophosphorolysis reaction. The apparatus can be configured to apply an electric field across the barrier so that nucleotide triphosphates are driven from the first compartment through the pore to the second compartment. The apparatus can be configured for measuring the electronic signature of a nucleotide triphosphate passing through the nanopore. Accordingly, a useful apparatus can include an electrical circuit capable of applying a potential and measuring an electrical signal across a barrier and nanopore. The methods may be carried out using a patch clamp or a voltage clamp.

A method of the present disclosure can be carried out using any suitable system in which a pore penetrates through a barrier. The barrier in many embodiments is preferably a lipid bilayer. Lipid bilayers can be made using methods known in the art, for example, as described in Montal and Mueller *Proc. Natl. Acad. Sci. USA* 69:3561-3566 (1972) or WO 2008/102120, each of which is incorporated herein by reference. Lipid bilayers can be formed from any of a variety of lipids including, but not limited to, phospholipids, glycolipids, cholesterol and mixtures thereof.

Exemplary nanopores that can be used include, for example, protein based nanopores such as alpha hemolysin nanopore, *mycobacterium smegmatis* porin A (MspA) and variants thereof. Alpha hemolysin nanopore and variants of the native nanopore that are particularly useful are described, for example, in US Pat. App. Pub. No. 2011/0229877 A1, or U.S. Pat. Nos. 6,916,665; 7,867,716; 7,947,454; or 8,105,846, each of which is incorporated herein by reference. MspA and variants of the native nanopore that are particularly useful are described, for example, in US Pat. App. Pub. No. 2012/0055792 A1, which is incorporated herein by reference. Solid state nanopores can also be useful including, for example, those described in U.S. Pat. Nos. 6,413,792; 7,444,053; or 7,582,490, each of which is incorporated herein by reference.

Detection of nucleotide triphosphates can exploit interaction with a nanopore that results in changes to the current flowing through the nanopore in a manner that is specific to each species of nucleotide triphosphate. For example, a first nucleotide triphosphate species may reduce the current flowing through the nanopore for a particular mean time period or to a particular extent. A second species of nucleotide triphosphate can be distinguished by virtue of a different mean time period or a different extent of current alteration when passing through the nanopore. Thus, different nucleotide triphosphate species can be distinguished based on distinctive alterations of the current flowing through a nanopore.

Nanopore detection can be carried out using any of a variety of apparatus known in the art including for example, those described in US Pat. App. Pub. Nos. 2011/0229877 A1; or 2012/0055792 A1; or U.S. Pat. Nos. 6,413,792; 6,916,665; 7,867,716; 7,444,053; 7,582,490; 7,947,454; or 8,105,846, each of which is incorporated herein by reference.

A polymerase that is used in an apparatus or method set forth herein can be present in solution such that it is relatively free to diffuse, at least within a reaction chamber or it can be relatively limited in its ability to diffuse by being attached to a solid phase support, nanopore, barrier or other component of a method or apparatus set forth herein. Limiting diffusion by attachment can provide an advantage of closely coupling the point of nucleotide triphosphate production (e.g. a polymerase catalyzing pyrophosphorolysis) with the point of nucleotide triphosphate detection (e.g. a nanopore through which the nucleotide triphosphates pass). A polymerase can be attached to a nanopore for example via a recombinant protein fusion to a subunit of a nanopore, chemical crosslinkage or adapter moiety. Useful methods for attaching polymerases to nanopores and polymerase-nanopore components are set forth, for example, in US Pat. App. Pub. Nos. 2011/0229877 A1; or 2012/0055792 A1; or U.S. Pat. No. 7,947,454, each of which is incorporated herein by reference.

A polymerase can be attached to a bead or other solid support that resides in a chamber where pyrophosphorolysis occurs. Chemical linkers that are useful for attaching polymerases to beads or solid supports include those that are commercially available, for example, from Thermo Fisher (Rockford, Ill.) or Sigma Aldrich (St. Louis, Mo.) or otherwise known in the art.

A polymerase can be attached to a barrier used in a nanopore sequencing apparatus. For example, in embodiments that use a lipid bilayer as the barrier, a lipophilic moiety can be attached to the polymerase to localize the polymerase in proximity to the bilayer due to interactions between the bilayer and lipophilic moiety. Exemplary lipophilic moieties include, but are not limited to, sterols or lipids. A further example of a lipophilic moiety is a membrane protein (or portion thereof) that can be attached to a polymerase, for example, via recombinant protein fusion. Linkages such as those set forth above for beads and other solid supports can be used to attach a polymerase to a barrier used in solid state nanopore systems.

A nucleic acid that is sequenced in a method set forth herein or present in a apparatus of the present disclosure can be in solution such that it is relatively free to diffuse or it can be relatively limited in its ability to diffuse by being attached to a solid phase support, nanopore, barrier or other component of a method or apparatus set forth herein. Attachments similar to those set forth above for polymerases can be used for nucleic acids. For example, a sterol, lipid or other lipophilic moiety can be attached to a nucleic acid to localize it to a lipid bilayer. An example is shown in FIG. 2, where the nucleic acid is localized to the membrane via a sterol moiety attached to the template strand. As exemplified by the figure, the nucleic acid can be attached via the template strand, for example, at the 5' end of the template strand. Attachment can also be made at a point on the template that is between the location where the polymerase is bound to the template and the 5' end of the template.

A lipophilic moiety can be attached to a nucleic acid using methods known in the art for attaching other moieties such as biotin or fluorophores. For example, a primer having the lipophilic moiety can be used in an amplification, primer extension, or ligation reaction. Alternatively or additionally, nucleotides having the moiety can be used in an extension or amplification reaction. If desired, a lipophilic moiety can be introduced prior to sequencing and during a sample preparation step, such as those set forth previously herein. For example, a targeted sequencing technique can be employed wherein a subset of target nucleic acid having desired sequences are to be selected from a more complex sequence background. In this example, a lipophilic moiety can be selectively introduced into the subset of target nucleic acids using the targeting technique and this can allow the targets to be selectively captured by a lipid bilayer, while other non-targeted sequences are washed away due to not having been modified to include the lipophilic moiety.

It can be beneficial in some embodiments to limit diffusion of both the polymerase and the nucleic acid with respect to a nanopore, for example, using one or more of the attachment means set forth above.

As set forth previously herein, a method of the present disclosure can include a step of contacting a target nucleic acid with a polymerase under conditions to sequentially remove nucleotides, thereby sequentially producing nucleotide triphosphates having a variety of different base moieties. The variety of different base moieties produced will depend on the content of the target nucleic acid that is contacted with the polymerase. For example, DNA typically includes the four common bases guanine, cytosine, adenine and thymine such that pyrophosphorolysis will produce deoxyguanidine triphosphate, deoxycytidine triphosphate, deoxyadenosine triphosphate and deoxythymidine triphosphate. In some cases the target nucleic acid may not include all four of these base types such that no more than 3, 2 or even 1 type of deoxynucleotide triphosphate will be produced by pyrophosphorolysis. In some cases, variants of one or more of these four base types can be present in the target DNA and accordingly pyrophosphorolysis can produce variant deoxynucleotide triphosphates having, for example, methyl, hydroxymethyl or other added moieties. Other variant bases known in the art such as those set froth herein can also be present in the deoxynucleotide triphosphates produced by pyrophosphorolysis.

Another example is RNA, which typically includes the four common bases guanine, cytosine, adenine and uracil such that pyrophosphorolysis will produce riboguanidine triphosphate, ribocytidine triphosphate, riboadenosine triphosphate and ribothymidine triphosphate. In some cases the target nucleic acid may not include all four of these base types such that no more than 3, 2 or even 1 type of ribonucleotide triphosphate will be produced by pyrophosphorolysis. Variant bases, such as those exemplified herein, for example, with respect to deoxynucleotide triphosphates, or otherwise known in the art, can be present in ribonucleotide triphosphates. Generally, the nucleotide triphosphates produced by pyrophosphorolysis (whether deoxynucleotide triphosphates or ribonucleotide triphosphates) will include one, at least two, at least three, at least four or more different base types.

A method of the present disclosure can be carried out under conditions that sequentially remove a number of nucleotides from a target nucleic acid, thereby sequentially producing that same number of nucleotide triphosphates. Furthermore, at least that same number of nucleotide triphosphates can be distinguished, for example, via passage through a nanopore, to allow determination of a sequence having a length that is at least equivalent to the number nucleotides removed from the target nucleic acid. In particular embodiments the number is at least 1, 2, 3, 4, 5, 10, 25, 50, 100, 200, 500, 1000, 10,000 or more up to and including the length of the target nucleic acid. Alternatively or additionally, the number may be no more than 1, 2, 3, 4, 5, 10, 25, 50, 100, 200, 500, 1000, or 10,000. The number may be, but need not be, between any two of these values. As set forth previously herein, a variety of techniques can be used to pause pyrophosphorolysis. This can provide for control of the length of sequence determined using embodiments of the present methods.

The number of nucleotide triphosphates released by pyrophosphorolysis and/or detected in a method set forth herein may be larger than the number of different types of nucleotide triphosphates detected. However, the order and number of the different nucleotide triphosphates detected can be correlated with the sequence of the nucleic acid.

In some embodiments it may be beneficial to repeatedly sequence a particular target nucleic acid. The repetition can be achieved, for example, by repeatedly processing a target nucleic acid molecule in a method set forth herein. For example, a method can include the steps of (a) contacting a target nucleic acid with a polymerase to sequentially remove nucleotide triphosphates from the target nucleic acid, wherein the nucleotide triphosphates that are removed have a variety of different base moieties; (b) distinguishing the different base moieties for the nucleotide triphosphates that are removed, thereby determining the sequence of the target nucleic acid; (c) regenerating at least a portion of the target nucleic acid; and repeating steps (a) and (b) using the regenerated target nucleic acid. The target nucleic acid can be regenerated for example by adding nucleotide triphosphates under conditions for the polymerase (or a newly added polymerase) to carry out a polymerization reaction to regenerate at least a portion of a strand of the target nucleic acid that was previously removed by pyrophosphorolysis. Typically pyrophosphate will be substantially absent during the polymerization reaction.

Figure 3:
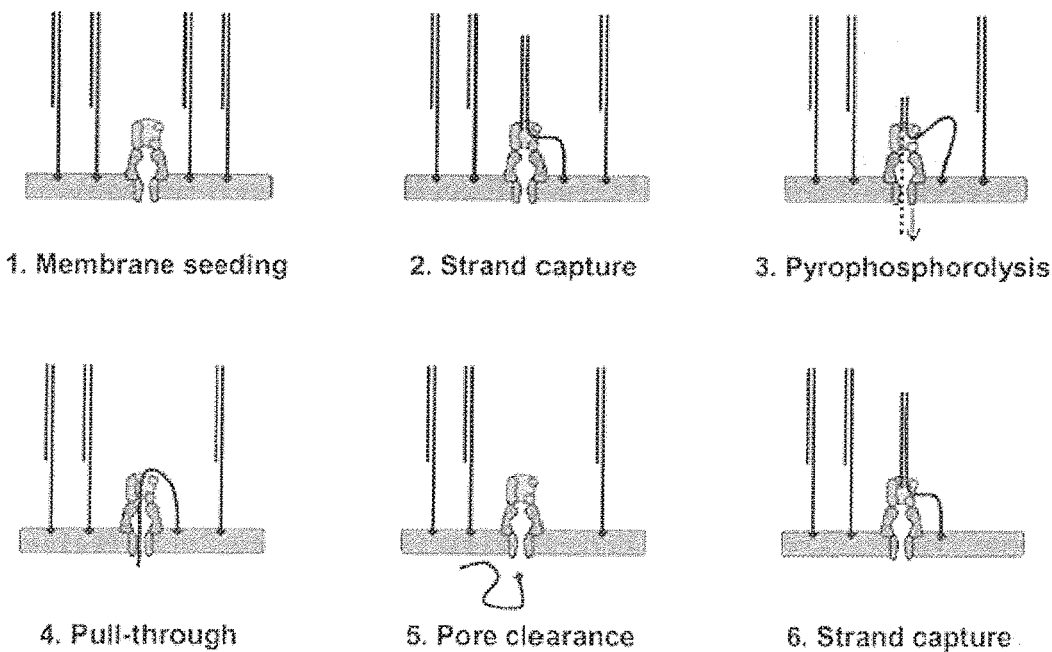
FIG. 3. shows pyrophosphorolytic sequencing with membrane seeding of multiple nucleic acid templates.

Alternatively or additionally to the repeated processing embodiment above, a target nucleic acid can be amplified or copied to create multiple copies that are processed using a method of the present disclosure. A diagrammatic example is shown in FIG. 3. Multiple copies of a double stranded template nucleic acid are localized to a barrier in a chamber having a nanopore-polymerase fusion (step 1), one of the strands is captured by the polymerase (step 2), pyrophosphorolysis-based sequencing occurs (step 3), the template strand, being single stranded, can then be pulled through the nanopore via electric force (step 4) until it is cleared from the chamber where the other copies of the nucleic acid remain (n.b. the other copies remain due to being double stranded and thus resistant to passage through the nanopore) (step 5), and then another copy of the double stranded template nucleic acid is captured to initiate repetition of steps 2 et seq. Any of a variety of methods known in the art for amplifying nucleic acids, such as those set forth previously herein, can be used to create the multiple copies of the target nucleic acid.

Although the system of FIG. 3 is exemplified for copies of a single template, it will be understood that nucleic acid species having different sequences can be used similarly. Thus, a variety of different double stranded nucleic acid species can be localized to a barrier in a chamber having a nanopore-polymerase fusion (step 1), a strand from a first species can be captured by the polymerase (step 2), pyrophosphorolysis-based sequencing can occur (step 3), the template strand of the first strand can then be pulled through the nanopore via electric force (step 4) until it is cleared from the chamber where the other nucleic acid species remain (step 5), and then another double stranded nucleic acid species can be captured to initiate repetition of steps 2 et seq.

The present disclosure also provides an apparatus that includes (a) a fluid impermeable barrier separating a first fluid reservoir from a second fluid reservoir; (b) a nanopore positioned in the fluid impermeable barrier to form a passage through which a nucleotide triphosphate can pass from the first fluid reservoir to the second fluid reservoir; and (c) a reaction mix in the first fluid reservoir, the reaction mix including a polymerase, target nucleic acid having two strands, and pyrophosphorolytic concentration of pyrophosphate. The components used in the apparatus can be one or more of those exemplified above in the context of various methods. Further components and configurations are exemplified below for purposes of illustration.

A fluid impermeable barrier can be configured to separate two reservoirs and to have a nanopore placed in the barrier to provide a fluid connection between the reservoirs. Exemplary nanopores and barriers are set forth above and in various references set forth above. Generally, the two reservoirs will be in fluid communication via a single nanopore. Thus, nucleotide triphosphates produced in one of the reservoirs will have one and only one fluid path to the second reservoir. The use of a single nanopore in this way allows for convenient measurement of each nucleotide triphosphate that passes from one reservoir to the other due to changes in electrical properties at the nanopore, barrier and/or reservoirs. However, it is also possible in some embodiments to include more than one nanopore in the barrier that separates two reservoirs. When multiple nanopores fluidly connect two reservoirs, the passage of nucleotide triphosphates can be measured at the individual nanopore using, for example, optical or electrical measurements that resolve each nanopore.

A reservoir can create a chamber where fluid remains contained for at least some of the time. For example, a chamber can be configured to form a well, cavity, compartment etc. that restricts the flow of fluid. Alternatively, a reservoir can be configured for fluid flow. For example, the reservoir can be configured as a tube, channel, or flow cell, thereby allowing flow of fluids for convenient delivery and removal of components used in a sequencing method. In particular embodiments, a first reservoir that contains template nucleic acid, polymerase and pyrophosphate will be configured for fluid flow, whereas the second reservoir, which is connected to the first chamber via a nanopore, can be configured as a chamber. The second reservoir need not be configured for fluid flow, but optionally can be.

The present disclosure provides multiplex embodiments. For example, the sequences for a plurality of target nucleic acids can be determined in parallel. A multiplex method can include the steps of (a) providing a plurality of target nucleic acids; (b) contacting each of the target nucleic acids with a polymerase to sequentially remove nucleotide triphosphates from each target nucleic acid, wherein the nucleotide triphosphates that are removed have a variety of different base moieties; and (c) distinguishing the different base moieties for the nucleotide triphosphates that are removed from each nucleic acid, thereby determining the sequences of the target nucleic acids.

A further example of a multiplex method is one that includes the steps of (a) providing a plurality of target nucleic acids each having two strands; (b) contacting each of the target nucleic acids with a polymerase under conditions to sequentially remove nucleotides from the first of each of the two strands by pyrophosphorolysis, thereby sequentially producing nucleotide triphosphates having a variety of different base moieties; and (c) distinguishing the different base moieties for the sequentially produced nucleotide triphosphates, thereby determining the sequence of the target nucleic acids.

A multiplex apparatus can include (a) a plurality of fluid impermeable barriers that each separate a first fluid reservoir from a second fluid reservoir; (b) a nanopore positioned in each of the fluid impermeable barriers to form a passage through which a nucleotide triphosphate can pass from the first fluid reservoir to the second fluid reservoir; and (c) a reaction mix in each of the first fluid reservoirs, each of the reaction mixes including a polymerase, target nucleic acid having two strands, and pyrophosphorolytic concentration of pyrophosphate.

The plexity (i.e. multiplex level) of a method or apparatus can be selected to satisfy a particular use. For example, the number of target nucleic acids that are processed or present together can be determined from the complexity of the sample to be evaluated. Exemplary complexity estimates for some of the genomes that can be evaluated using methods or apparatus of the present disclosure are about 3.1 Gbp (human), 2.7 Gbp (mouse), 2.8 Gbp (rat), 1.7 Gbp (zebrafish), 165 Mbp (fruit fly), 13.5 Mbp (S. cerevisiae), 390 Mbp (fugu), 278 Mbp (mosquito) or 103 Mbp (C. elegans). Those skilled in the art will recognize that genomes having sizes other than those exemplified above including, for example, smaller or larger genomes, can be used in a method of the invention. Typically a nucleic acid sample is fragmented prior to use. The number of fragments to be handled in parallel will depend on the complexity of the genome, the average fragment size and the desired coverage. For example, 1× coverage of a human genome (3.1 Gbp) that is fragmented to an average size of 1000 nucleotides can be achieved using plexity of 3 million fragments (i.e. ((3.1 billion/1000)×1)=1 million). Using similar calculations one can determine that a plexity of 30 million fragments (of 1000 nucleotides each) is sufficient to provide 30× coverage of a human genome.

The methods and apparatus set forth herein can be configured at a plexity level sufficient to provide at least 1×, 2×, 5×, 10×, 20×, 30×, 50× or more coverage of any of a variety of genomes including, but not limited to, those exemplified herein. The plexity can be a function of the number of various components set forth herein such as the number of target nucleic acid fragments as exemplified above. Other components that can be multiplexed include, for example, the number of nanopores used, the number of polymerases, the number of chambers having a barrier and nanopore etc. The multiplex level of these or other components can be, for example, at least 2, 5, 10, 100, $1\times10^3$, $1\times10^4$, $1\times10^5$, $1\times10^6$, $1\times10^9$, or higher. Alternatively or additionally, the multiplex level can be selected to be no more than 2, 5, 10, 100, $1\times10^3$, $1\times10^4$, $1\times10^5$, $1\times10^6$, or $1\times10^9$.

Throughout this application various publications, patents and patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. A method for determining the sequence of a target nucleic acid, comprising:
    (a) providing a target nucleic acid having two strands;
    (b) contacting the target nucleic acid with a polymerase under conditions to sequentially remove nucleotides from a first strand of the two strands by pyrophosphorolysis, thereby sequentially producing single nucleotide triphosphates having a variety of different base moieties, wherein the conditions to sequentially remove single nucleotide triphosphates from a first strand of the two strands by pyrophosphorolysis comprise contacting the polymerase with a pyrophosphorolytic concentration of pyrophosphate; and
    (c) distinguishing the variety of different base moieties for the sequentially produced single nucleotide triphosphates, wherein the distinguishing of the variety of different base moieties for the sequentially produced single nucleotide triphosphates comprises passing the single nucleotide triphosphates through a nanopore and distinguishing the single nucleotide triphosphates by detecting variations in an ionic current flowing through the nanopore, thereby determining the sequence of the target nucleic acid, wherein the pyrophosphorolysis is paused and then resumed between (b) and (c), to produce the single nucleotide triphosphates at a desired rate.

2. The method of claim 1, wherein the polymerase is attached to the nanopore.

3. The method of claim 1, wherein the nanopore comprises a protein nanopore that is embedded in a membrane.

4. The method of claim 3, wherein a second strand of the two strands of the target nucleic acid is attached to the membrane.

5. The method of claim 1, wherein the nanopore comprises a solid state nanopore.

6. The method of claim 1, wherein the pyrophosphorolytic concentration of pyrophosphate comprises a concentration of at least 100 μM.

7. The method of claim 1, wherein the pausing the sequential removal of the single nucleotide triphosphates is by removing pyrophosphate from contact with the polymerase and then resuming the sequential removal of the single nucleotide triphosphates is by contacting the polymerase with pyrophosphate.

8. The method of claim 1, wherein the variety of different base moieties comprises at least two different species of base moieties and at most four different species of base moieties.

9. The method of claim 8, wherein the sequence that is determined is longer than four nucleotides.

10. The method of claim 1, wherein the variety of different base moieties comprise naturally occurring adenine, guanine, cytosine or thymine.

11. The method of claim 1, wherein at least one of the variety of different base moieties comprises a moiety that is non-naturally occurring in DNA or RNA.

12. The method of claim 1, wherein the target nucleic acid is DNA.

13. The method of claim 12, wherein at least one of the variety of different base moieties comprises a moiety that is non-naturally occurring in DNA.

14. The method of claim 12, wherein at least one of the variety of different base moieties comprises 5-methyl cytosine or 5-hydroxymethylcytosine.

15. The method of claim 14, wherein the 5-methyl cytosine or 5-hydroxymethylcytosine is distinguished from cytosine, thereby facilitating an epigenetic analysis.

16. The method of claim 1, wherein the polymerase lacks 3' to 5' exonuclease activity.

17. The method of claim 1, wherein the target nucleic acid is a heteroduplex formed by a DNA strand and RNA strand.

18. The method of claim 1, wherein the conditions to sequentially remove nucleotide triphosphates from one of the two strands by pyrophosphorolysis comprise contacting the polymerase with a pyrophosphorolytic concentration of a pyrophosphate analog.

19. The method of claim 18, wherein the pyrophosphate analog comprises pyrophosphate having an additional moiety.

20. The method of claim 18, wherein the pyrophosphate analog comprises pyrovanadate.

21. The method of claim 1, wherein at least 10 nucleotides are sequentially removed from the first strand of two strands and distinguished by passing through the nanopore.

* * * * *